United States Patent [19]

Steinhauser et al.

[11] Patent Number: 5,558,776

[45] Date of Patent: Sep. 24, 1996

[54] PROCESS FOR THE MANUFACTURE OF A COMPOSITE PLASMA MEMBRANE AND USE THEREOF

[75] Inventors: Hermann Steinhauser, Saarbrücken; Hartmut Brüschke, Nussloch; Guido Ellinghorst, Overath; Andreas Hübner, Unna, all of Germany

[73] Assignee: Deutsche Carbone, AG, Frankfurt, Germany

[21] Appl. No.: 324,344

[22] Filed: Oct. 17, 1994

Related U.S. Application Data

[62] Division of Ser. No. 135,402, Oct. 13, 1993, abandoned.

[30] Foreign Application Priority Data

Oct. 13, 1992 [DE] Germany .................. 42 34 521.9

[51] Int. Cl.⁶ .................................................. B01D 61/36
[52] U.S. Cl. ...................................... 210/640; 210/500.27
[58] Field of Search ................................ 210/640, 651, 210/652, 490, 500.27; 264/22

[56] References Cited

U.S. PATENT DOCUMENTS

| | | | |
|---|---|---|---|
| 3,657,113 | 4/1972 | Stancell et al. | 210/23 |
| 3,775,308 | 11/1973 | Yasuda | 210/23 |
| 4,032,440 | 6/1977 | Yasuda | 210/23 |
| 4,774,365 | 9/1988 | Chen et al. | 568/697 |
| 4,802,988 | 2/1989 | Bartels et al. | 210/640 |
| 4,806,246 | 2/1989 | Nomura | 210/651 |
| 4,877,529 | 10/1989 | Pasternak et al. | 210/500.37 |
| 4,960,519 | 10/1990 | Pasternak et al. | 210/640 |
| 5,030,355 | 7/1991 | Schucker | 210/640 |
| 5,238,613 | 8/1993 | Anderson | 264/22 |
| 5,248,427 | 9/1993 | Spiske et al. | 210/640 |
| 5,360,923 | 11/1994 | Nickel et al. | 558/277 |

*Primary Examiner*—Frank Spear
*Attorney, Agent, or Firm*—Banner & Allegretti, Ltd.

[57] ABSTRACT

Process for the manufacture of composite plasma membranes with the production of a pore-free impermeable polymer layer on a porous substrate through the plasma polymerization of a gaseous mixture, said gaseous mixture containing a hydrocarbon as the matrix-forming component and a nitrogen-, silicon-, sulphur- or phosphorus-containing inorganic compound as the non-matrix-forming component and an oxygen-containing compound, by means of glow discharge in an electrical alternating field. The pore-free impermeable polymer layer is produced directly on a porous substrate without the use of an impermeable intermediate layer, said porous substrate having a pore diameter of less than 100 nm on the side facing the pore-free polymer layer. The composite plasma membranes are used for separating $C_1$–$C_3$ alkanols from mixtures thereof with other organic liquids using the method of pervaporation.

18 Claims, No Drawings

PROCESS FOR THE MANUFACTURE OF A COMPOSITE PLASMA MEMBRANE AND USE THEREOF

This application is a division of application Ser. No. 08/135,402, filed Oct. 13, 1993, now abandoned.

The present invention relates to a process for the manufacture of a composite plasma membrane and use thereof to separate $C_1$–$C_3$ alcohols from mixtures thereof with organic liquids by means of pervaporation.

It is known that liquid mixtures can be broken down into their components or that a component can be separated from a liquid mixture. The processes known for this purpose are, for example, distillation, rectification, extraction, absorption and adsorption. The separation effect of said processes is based on the different distribution of the components in phases that are in equilibrium with one another. The person skilled in the art will also know, however, that such processes are subject to certain limitations. For instance, simple distillation or rectification cannot be used or can be used only with additional effort to separate azeotropic mixtures or mixtures of components with similar boiling points. Corresponding limitations apply to processes of extraction and adsorption.

It is further known that liquid mixtures can be separated by means of membrane-type processes. Since membrane-type separation processes employ for separation not the different distribution of components in different phases, but the different rate of mass transfer of the component through a membrane, they can often be used particularly effectively in cases where equilibrium-type separation processes fail or deliver unsatisfactory results. The processes of pervaporation and vapor permeation will be known as examples to the person skilled in the art. In said process, the liquid mixture (infeed mixture), in liquid or vaporous phase, preferably in the form of saturated vapour, is brought into contact with a first side of a non-porous membrane. At least one component of the mixture has a higher permeation capacity in the membrane than the other components. As long as a gradient is maintained in the partial vapour pressure of said component between the first side, the infeed side, and a second side, the permeate side, of the membrane, a mass stream will flow through the membrane. At the permeate side, there is thus a permeate stream with a higher concentration of the component with the better permeation capability than the infeed mixture; from the infeed side it is possible to draw off a mass stream in which the concentration of the component with the better permeation capability is lower than in the original infeed mixture. The vaporous permeate can be condensed or continuously removed from the permeate side of the membrane by other methods known to the person skilled in the art.

EP-A-0 096 339, 0 307 636 and 0 442 557 as well as U.S. Pat. Nos. 4,802,988 and 4,892,661, for example, describe membranes that are suitable for separating water from mixtures thereof with organic liquids by means of pervaporation. The non-porous separation layer of said membrane consists of polyvinyl alcohol.

U.S. Pat. Nos. 4,670,146, 4,728,429 and 4,865,743 as well as EP-A-0 221 171 describe membranes for the same application; the non-porous separation layer has ion-exchanging properties.

U.S. Pat. Nos. 4,590,098, 4,618,534 and 4,925,562 as well as EP-A-0 254 758 describe so-called hydrophobic membranes, which are permeated by preferably organic components, whereas they retain water and are thus suitable for separating volatile, organic substances from water.

U.S. Pat. Nos. 5,039,422, 5,039,418, 5,039,417, 5,030,355, 5,019,660, 5,012,035, 4,944,880 and 4,802,987 as well as DE-A-2 627 629 describe membranes with which aromatic hydrocarbons can be separated from aliphatic hydrocarbons.

U.S. Pat. No. 4,774,365 describes a process whereby surplus methanol can be separated from ethers and a $C_4$ to $C_7$ cut in the manufacture of methyl tertiary butyl ether (MTBE) and tertiary amyl methyl ether. Cited as suitable examples are membranes made of cellulose acetate, polyvinyl alcohol, polysulfone, silicone rubber and polysubstituted acetylenes, with membranes made of cellulose acetate and polyvinyl alcohol being preferred. No further details are given about the cellulose-acetate membranes.

U.S. Pat. No. 4,877,529 describes a non-porous ion-exchange membrane, with disclosure being made of a per-fluorated acidic ion exchanger, the pendant acid group of which is neutralized by quaternary ammonium salt; the alkyl groups of the ammonium ion each contain less than 4 C-atoms. This membrane is said to be particularly suitable for separating methanol, in the case of low concentrations of methanol, from mixtures thereof with MTBE.

U.S. Pat. No. 4 960 519 describes a process for separating methanol from mixtures thereof with oxygen-containing compounds, the latter comprising organic ethers, aldehydes, ketones and esters. The disclosed membrane has a non-porous separation layer consisting of a mixture of polyvinyl alcohol and polyacrylic acid on a polyacrylonitrile support layer.

DE-A-4 029 349 describes a process for separating water from a mixture containing water and alcohol and/or carboxylic acids and/or carboxylic-acid esters, wherein use is made of a membrane obtained by plasma polymerization. Preferably, use is made of composite membranes consisting of a pore-free, impermeable layer on a porous substrate material, with the impermeable, pore-free layer being produced by plasma polymerization. Said layer is permeated preferably by water, while alcohols and other organic components are retained.

The invention therefore relates to a process for the manufacture of a composite plasma membrane comprising the formation of a pore-free impermeable polymer layer on a porous substrate by plasma polymerization of a gaseius mixture, said gaseous mixture containing one or more hydrocarbons as the matrix-forming component, and one or more nitrogen-, silicon-, sulphur- or phosphorus-containing inorganic compounds as the non-matrix-forming component, by means of glow discharge in an electrical alternating field, characterized in that the initial gaseous mixture additionally contains an oxygen-containing compound, with the pore-free impermeable polymer layer being produced directly on a porous substrate without the use of an impermeable intermediate layer, said porous substrate having a pore diameter of less than 100 nm on the side facing the pore-free polymer layer. The invention relates further to the use of said composite plasma membrane for separating $C_1$–$C_3$ alcohols from mixtures thereof with organic liquids by means of pervaporation.

Plasma polymerization

The person skilled in the art will know of the process by which thin layers are applied to a substrate by plasma polymerization. Two electrodes are installed opposite one another in an evacuatable container, between which electrodes a direct- or alternating-current glow discharge is ignited, with the pressure in the evacuated container being generally between $10^{-3}$ and 20 mbar. Produced by collision processes in the discharge space between the electrodes are free electrons, positively and negatively charged ions, excited atoms and molecules as well as radicals, which are able to react with one another and with the surfaces of the container and of the electrodes. If, in particular, the gaseous mixture forming the plasma contains organic molecules, these may likewise become fragmented and, with the inclusion of non-organic components, may react off in diverse manner. The resulting substances are known as plasma polymers. These differ from polymers formed by conventional reactions in that it is not possible to identify in them any repeated monomer units, but there is a three-dimensional network of different atoms and atom groups.

Such plasma polymers are used to modify, surfaces, for example in order to alter corrosion properties, hardness, friction coefficients or optical properties. There has also been no shortage of attempts to form, by means of plasma polymers, general or selective barrier layers and to employ the latter for separation purposes. Thus, U.S. Pat. No. 3,657,113 describes a process for at least the partial separation of fluid components from fluid mixtures by preferred diffusion of said components through a pore-free layer of a cross-linked plasma polymer. The plasma polymer is applied to a layer of an amorphous polymer at a pressure of 0.1–5 torr and in a thickness of between 0.03 and 2 µm. Cited as preferred amorphous polymers are polyphenylene oxide and siloxanes and copolymers thereof. Preferred as plasma gas are aromatic compounds, nitriles and polyunsaturated compounds; the thus obtained membranes separate hydrogen from hydrogen-methane mixtures. EP-A-0 134 055 describes a composite membrane with pore-free separation layer, with the pore-free, selective separation layer being applied in a thickness of less than 0.1 µm to an impermeable polymer layer of a conventional polymer. The layer of the conventional polymer is between 0.01 and 5 µm thick, consisting preferably of polydimethyl siloxane and being carried by a porous substructure. The selective separation layer formed by plasma polymerization is silicone-free, but may, in turn, also carry, a thin protective layer on the side facing the mixture to be separated, said protective layer consisting preferably of the same material as the polymer layer to which the plasma layer has been applied, e.g. silicone. Membranes of this type are said to be suitable preferably for the separation of carbon dioxide and methane.

According to the invention, the, plasma polymer forming the selective separation layer is deposited in an apparatus consisting of an evacuatable container with pressure regulation and controllable gas-inlet systems as well as of devices for measuring the total pressure and partial pressures of the gaseous components. Positioned opposite one another in the container are two electrodes, one of which is grounded. On one of the electrodes there is the porous substrate on which the plasma-polymer layer is deposited. Between the two electrodes there is an electrical alternating field with frequencies between 10 kHz and 20 GHz, with controllable electrical power of the alternating field. In a preferred embodiment, a roll of the porous substrate is drawn at regulated speed over an electrode, with the result that there is a continuous deposition of a plasma-polymer layer. Surprisingly, it has been demonstrated that pore-free, impermeable plasma-polymer layers can be deposited directly on a porous substrate without the need first of all to apply an impermeable intermediate layer between porous substrate and plasma-polymer layer. According to the present invention, porous materials of carbon, metal, ceramic or polymer may be employed as substrates, with use being made preferably of substrates in the form of porous membranes with an asymmetrical pore structure, e.g. of polyacrylonitrile, polysulfone or other polymers. An essential feature of the invention is that, on the surface on which the plasma-polymer layer is deposited, these substrates have pores with a diameter of less than 100 nm. Larger pores cannot be safely bridged with the plasma-polymer layer, this resulting in imperfections. Preferably, the pores are of a size as uniform as possible, with an average pore width of between 5 and 40 nm. Porous membranes with an asymmetrical pore structure are effectively known and, for example, are employed on a large scale in ultrafiltration. Normally, they are of a thickness between 30 and 150 µm. Commercially available membranes additionally have a backing consisting of a fleece or fabric, in which case they are of a total thickness of between 100 and 300 µm.

The gaseous mixture in the region of the glow discharge between the electrodes, from which gaseous mixture the plasma polymer is formed, contains at least one matrix-forming and at least one non-matrix-forming component as well as, additionally, an oxygen-containing component.

All hydrocarbons having a vapour pressure of at least 0.5 mbar at 50° C. may be used as the matrix-forming component. Examples of suitable hydrocarbons are aliphatic hydrocarbons with between 1 and 12 C-atoms, such as methane, butane or decane, or aromatic hydrocarbons, such as benzene or toluene. Low-molecular hydrocarbons with at least one C—C double bond are preferred, with ethene and propene being particularly preferred.

The non-matrix-forming component comprises inorganic compounds containing nitrogen, silicon, sulphur or phosphorus and having a vapour pressure of at least 1 mbar at 50° C. Examples of suitable compounds are hydrogen compounds, such as ammonia, silanes, hydrogen sulphide or phosphines, or oxides of nitrogen, sulphur or phosphorus, such as nitrous oxide, sulphur dioxide or sulphur trioxide. Nitrogen-containing compounds, such as ammonia, hydrazine or nitrogen, are preferred, with ammonia being particularly preferred.

Suitable oxygen-containing components are oxygen, carbon dioxide, carbon monoxide and water, with oxygen, carbon dioxide and water being preferred.

Matrix-forming and non-matrix.-forming components are generally used in a molar ratio of between 0.2 and 5, preferably between 0.5 and 1.5.

The oxygen-containing component is generally used in a molar ratio, with reference to the sum of matrix-forming and non-matrix-forming components, of between 0.05 and 0.3, preferably between 0.1 and 0.2. The pressure in the plasma reactor is generally between $10^{-3}$ and 10 mbar, preferably between 0.1 and 1 mbar. The electrical field operates generally in the range between 10 kHz and 5 GHz, preferably between 20 kHz and 14 MHz. Generally, use is made of an electrical power of between 0.01 and 3 watts per cm2 of electrode surface area, preferably between 0.1 and 1 watt per cm2. The deposition time is generally between 2 seconds and 1 hour, preferably between 20 seconds and 10 minutes. The thickness; of the deposited plasma-polymer layer is generally between 0.1 and 2 µm, preferably between 0.5 and 1 µm.

The membranes manufactured according to the invention are used preferably for separating $C_1$–$C_3$ alkanols from mixtures thereof with organic liquids by means of pervaporation, with the liquid mixture to be separated being supplied in liquid or vaporous phase on the infeed side of the membrane. For this reason, the term "vapour permeation" is employed also for herein-described membrane-type sedation process instead of the expression "pervaporation". The herein-used expression "pervaporation" should be understood in this comprehensive sense.

The $C_1$–$C_3$ alkanols are methanol, ethanol, propanol and isopropanol. These alkanols are present in the initial mixture together with other organic compounds, the latter preferably being hydrocarbons or compounds containing hetero-atoms, with the hetero-atom preferably being oxygen. Examples of mixture components are aliphatic hydrocarbons, such as hexane or heptane, aromatic hydrocarbons, such as benzene or toluene, as well as, in particular, oxygen-containing compounds, such as ethers, aldehydes, ketones, esters and carboxylic acids. Of particular interest is the separation of alkanols from those mixtures in which azeotropes are formed and which, therefore, are very difficult to separate using other conventional processes. A special area of application is the separation of the corresponding alkanol in the manufacture of alkyl tertiary butyl ethers.

Surprisingly, it has been demonstrated that membranes manufactured according to the invention have a high permeability for $C_1$–$C_3$ alkanols, whereas other organic components, such as hydrocarbons and hydrocarbons containing hetero-atoms, are retained.

The examples illustrate the invention. All percentages are given in weight percent.

EXAMPLE 1 (control example)

In an evacuatable vessel provided with pressure regulation and controllable infeeds for gaseous or vaporous matrix-forming, non-matrix-forming and oxygen-containing components and comprising two electrodes positioned opposite one another, between which electrodes it is possible to apply an electrical alternating field, a porous membrane of polyacrylonitrile with an asymmetrical pore structure is attached to one of the electrodes. On the "fine side", the membrane has pores with an average pore diameter of 20 nm. The vessel is evacuated to a total pressure of $10^{-4}$ mbar. As the matrix-forming gas, ethylene is admitted at a rate of 1.34 mmol/min., with ammonia being admitted as the non-matrix-forming gas at a rate of 1.65 mmol/min. The total pressure is held at 0.4 mbar. An electrical discharge with a frequency of 37 kilohertz is ignited between the electrodes, which each have a surface area of 630 $cm^2$, with a power of 500 watts being used. After a deposition time of 5 minutes, the gas infeed and the electrical alternating field are switched off, the reactor is flooded with air and the membrane is removed.

In a pervaporation test, the performance of this membrane was tested at 50° C. with an infeed mixture of n-heptane and methanol. With a methanol concentration of 5.4% in the infeed, a flow of 0.19 kg/m2h with a concentration of 45% methanol was measured in the permeate; with 1.8% methanol in the infeed, the flow is 0.096 kg/$m^2$h, with the permeate containing 18% methanol.

EXAMPLE 2

A plasma-polymer membrane is manufactured as described in example 1. The gas flows of the matrix-forming and non-matrix-forming components are unchanged, as is the total pressure. In addition, oxygen is admitted at a rate of 0.38 mmol/min; the electrical power is 215 W at a frequency of 37 kHz, with the treatment time being 5 minutes. A separation layer is obtained with a thickness of 0.5 µm. In a pervaporation test as in example 1, with 5.1% methanol in the infeed, one obtains a flow of 2.2 kg/$m^2$h and a methanol concentration in the permeate of 99.4%.

EXAMPLE 3

A membrane as in example 1 is manufactured. Ethene is used as the matrix-forming gas at a rate of 1.27 mmol/min, with ammonia being used as the non-matrix-forming gas at a rate of 1.7 mmol/min. In addition, carbon dioxide is added at a rate of 0.22 mmol/min, with the total pressure being set to 0.8 mbar. At 37 kHz, 500 W is maintained for 3 minutes. The membrane obtained has a separation layer with a thickness of 0.6 µm and, in a pervaporation test as in example 1, with 3.4% methanol in the infeed, yields a flow of 1.3 kg/$m^2$h with a permeate concentration of 98.9% methanol.

EXAMPLE 4

A membrane is manufactured as in example 1. Used as the substrate is an asymmetrical polysulfone ultrafiltration membrane, the fine side of which has pores with an average pore diameter of 30 nm. Ethene is admitted at a rate of 1.34 mmol/min, with nitrogen being admitted as the non-matrix-forming component at a rate of 0.8 mmol/min, with water being additionally admitted at a rate of 0.25 mmol/min. With a total pressure of 0.8 mbar, a power of 425 W at 37 kHz and a treatment time of 5 minutes, a membrane was obtained with a separation-layer thickness of 0.5 µm. In a pervaporation test as in example 1, with 2.4% methanol in the infeed, the membrane yielded a flow of 0.2 kg/$m^2$h with a permeate concentration of 96.9% methanol.

EXAMPLE 5

As in example 1, a plasma-polymer layer was deposited on a porous asymmetrical polyacrylonitrile ultrafiltration membrane with an average pore radius on the fine side of 14 nm. Propene was admitted as the matrix-forming gas at a rate of 1.3 mmol/min, with ammonia being admitted as the non-matrix-forming component at a rate of 1.6 mmol/min, with 0.4 mmol/min oxygen additionally being admitted. At a total pressure of 0.8 mbar and a power of 215 W at 35 kHz, the treatment time was 5 minutes. A membrane with a separation-layer thickness of 0.5 µm was obtained. A mixture of 70.1% ethyl tertiary butyl ether and 29.9% ethanol was used at 50° C. for the pervaporation test. The flow through the membrane was 1.13 kg/$m^2$h, with the permeate containing 94.8% ethanol.

EXAMPLE 6

The membrane from example 5 was tested with a mixture of 70% tetrahydrofuran and 30% methanol. At 70° C. a flow of 5.8 kg/$m^2$ was measured, with the permeate containing 98.5% methanol.

What is claimed is:

1. A process for separating $C_1$–$C_3$ alkanols from mixtures thereof with other organic liquids by pervaporation using a composite plasma membrane, said method comprising:

obtaining a composite plasma membrane prepared by forming a pore-free impermeable plasma-polymer layer on a porous substrate by plasma polymerization of a plasma-forming gaseous mixture by means of glow discharge in an electrical alternating field, said plasma-forming gaseous mixture containing one or more hydrocarbons as a matrix-forming component, one or more nitrogen-, silicon-, sulphur- or phosphorus-containing inorganic compounds as a non-matrix-forming component, and an oxygen-containing component, said pore-free polymer layer being produced directly on the porous substrate without the use of an impermeable intermediate layer, the pores on the surface of said porous substrate on which the plasma-polymer layer is formed having a pore diameter of less than 100 nm, separating a mixture of a $C_1$–$C_3$ alkanol and other organic liquid by passing said $C_1$–$C_3$ alkanol through said composite plasma membrane from the pore-free side thereof, and recovering a permeate containing said $C_1$–$C_3$ alkanol.

2. The process of claim 1 wherein said oxygen-containing component of said plasma-forming gaseous mixture is oxygen, carbon dioxide or water.

3. The process of claim 1 wherein said porous substrate is an asymmetrical membrane having an average pore diameter of from 5 to 40 nm on the fine side thereof.

4. The process of claim 1 wherein the matrix-forming component of said plasma-forming gaseous mixture is ethene or propene.

5. The process of claim 1 wherein the non-matrix-forming component of said plasma-forming gaseous mixture is ammonia or nitrogen.

6. The process of claim 1 wherein the frequency of said electrical alternating field is between 20 kHz and 14 MHz.

7. The process of claim 1 wherein said glow discharge employs an electrical power of between 0.1 and 1 W per $Cm^2$ electrode surface area.

8. The process of claim 1 wherein a pressure of between 0.1 and 1 mbar is set for the plasma-forming gaseous mixture.

9. The process of claim 1 wherein the other organic liquid is a hydrocarbon.

10. The process of claim 9 wherein said hydrocarbon is an aliphatic hydrocarbon or an aromatic hydrocarbon.

11. The process of claim 10 wherein said hydrocarbon contains a hetero-atom.

12. The process of claim 11 wherein said hydrocarbon contains oxygen.

13. The process of claim 12 wherein said hydrocarbon is an ether, an aldehyde, a ketone, an ester or a carboxylic acid.

14. The process of claim 1 wherein said alkanol is separated from an azeotropic mixture.

15. The process of claim 1 wherein said alkanol is separated from a mixture containing a corresponding alkyl tertiary butyl ether.

16. The process of claim 15 wherein ethanol is separated from ethyl tertiary butyl ether.

17. The process of claim 1 wherein methanol is separated from a mixture containing methanol and tetrahydrofuran.

18. The process of claim 1 wherein said mixture to be separated is separated by said composite plasma membrane in the vapor phase.

* * * * *